United States Patent [19]

Narishige

[11] Patent Number: 4,901,446
[45] Date of Patent: Feb. 20, 1990

[54] APPARATUS FOR FINELY ACTUATING A GLASS ELECTRODE OR THE LIKE

[75] Inventor: Eiichi Narishige, Tokyo, Japan

[73] Assignee: Narishige Scientific Instrument Laboratory, Ltd., Tokyo, Japan

[21] Appl. No.: 218,241

[22] Filed: Jul. 13, 1988

[30] Foreign Application Priority Data

Apr. 20, 1988 [JP] Japan ............................. 63-53290[U]

[51] Int. Cl.$^4$ ............................................. G01B 5/00
[52] U.S. Cl. ...................................... 33/572; 33/613; 33/503; 33/626
[58] Field of Search ................. 33/572, 613, 503, 626, 33/568

[56] References Cited

U.S. PATENT DOCUMENTS 4,272,892  6/1981  Rose ...................................... 33/572
4,565,094  7/1986  Sedgewick ........................... 33/568

Primary Examiner—Harry N. Haroian
Attorney, Agent, or Firm—Cushman, Darby & Cushman

[57] ABSTRACT

An apparatus for finely actuating a glass electrode or the like tool includes a movable portion adapted to be vertically displaced with the aid of a vertical actuating mechanism. A Y-coordinate slider is mounted on the movable portion to slide in the Y-coordinate direction and a X-cordinate slider is in turn mounted on the Y-coordinate slider to slide in the X-coordinate direction. A Y-coordinate thrusting rod is provided in the movable portion to thrust a Y-coordinate lever rod disposed between the Y-coordinate thrusting rod and the Y-coordinate slider, while a X-coordinate thrusting rod is likewise provided in the movable portion to thrust a X-coordinate lever rod disposed between the X-coordinate thrusting rod and the Y-coordinate slider. This enables a lever ratio to be reduced to a fraction of the ratio. Two return springs are provided so as to allow both the Y-coordinate slider and X-coordinate slider to resume their original position. One of them is resiliently bridged between the movable portion and the Y-coordinate slider and the other one is resiliently bridged between the Y-coordinate slider and the X-coordinate slider.

17 Claims, 4 Drawing Sheets

APPARATUS FOR FINELY ACTUATING A GLASS ELECTRODE OR THE LIKE

BACKGROUND OF THE INVENTION

1. Field of the Invention

The present invention relates to an apparatus for finely actuating a glass electrode or the like tool for the purpose of treating a cell to obtain data therefrom by measurements more particularly, the present invention is directed to a finely actuatable apparatus preferably employable for a so-called patch clamping system for measuring the status of a cell while a glass electrode or the like tool is brought in contact with a channel on the cell membrane.

2. Prior Art

As an apparatus for measuring the status of a cell in the field of biotechnology, there is generally known such an apparatus of the type including a glass electrode adapted to be inserted into the interior of a cell to extract biological electricity in the cell via an electrolyte filled in the glass electrode.

However, since a glass electrode or the like tool should be inserted into the interior of a cell, the conventional apparatus has a problem in that the cell is damaged. Accordingly, the cell's live state terminates within a short period of time, with the result that functions of the cell can not be measured for a long period of time.

To solve the foregoing problem, a so-called patch clamp system has been developed in recent years to assure that functions of a cell can be measured for a long period of time. According to the patch clamp system, a glass electrode is aligned with a predetermined channel on the cell membrane to come in contact with it without any need of inserting the glass electrode into the interior of the cell so that the biological electricity of the cell can be measured through the channel for a long period of time. Here, a channel on the cell membrane refers to a position where only necessary materials are introduced into the interior of the cell therethrough and some materials in the interior of the same are discharged to the outside therefrom.

To locate a glass electrode in correct alignment with a channel on the cell membrane, an apparatus for finely actuating the glass electrode is used. The apparatus is intended to finely displace the glass electrode in the vertical direction as viewed from the above (hereinafter referred to as a direction of Y-coordinate), in the lateral direction (hereinafter referred to as a direction of X-coordinate) and in the direction of height (hereinafter referred to as Z-coordinate) by a distance in the order of microns in unit. A conventional apparatus can be generally classified into one of three types, that is, a mechanical type, a hydraulic type or an electrical type. An apparatus of the mechanical type is classified further into two types. One type is such that a plate for the X-coordinate, a plate for the Y-coordinate and a plate for the Z-coordinate are successively jointed to one after another. Each of the plates, for the X-coordinate, the Y-coordinate and the Z-coordinate are thrust against the resilient force of a leaf spring with the use of a lever rod so that a glass electrode mounted on the final plate is finely displaced in the direction of the X-coordinate, in the direction of the Y-coordinate and in the direction of the Z-coordinate.

The other mechanical type is such that a spherical member adapted to eccentrically rotate a tilting operation performed by a lever, thrusts sliders in the direction of the X-coordinate and in the direction of the Y-coordinate. An apparatus of the hydraulic type is so constructed that sliders are finely displaced in the direction of the X-coordinate, in the direction of the Y-coordinate and in the direction of the Z-coordinate by utilizing a plurality of micro-hydraulic cylinders. Of course, an arrangement is made such that a glass electrode is firmly mounted on one of the sliders.

On the other hand, an apparatus of the electrical type is so constructed that a glass electrode is finely displaced in the direction of the X-coordinate, in the direction of the Y-coordinate and in the direction of the Z-coordinate by utilizing step motors.

However, each of the conventional apparatuses as described above has the following problems.

Specifically, an apparatus of the type including a combination of lever rods and a leaf spring with plates operable in the direction of the X-coordinate, in the direction of the Y-coordinate and in the Z-coordinate has a problem in that each of the plates performs arcuate movement but fails to perform fine linear movement. This problem occurs when the plates are thrust in the direction of the X-coordinate, in the direction of the Y-coordinate and in the direction of the Z-coordinate against the resilient force of the leaf springs by operating the lever rods. Since the glass electrode does not perform linear movement but performs arcuate movement in response to actuation of the lever rods in predetermined directions, it is not easy to locate the glass electrode in correct alignment with a predetermined channel on the cell membrane.

Further, an apparatus of the type including a combination of levers for tilting operation with spherical members adapted to eccentrically rotate is so constructed that sliders are displaced in two directions, that is, in the direction of the X-coordinate and in the direction of the Y-direction. Moreover the sliders are thrust under the effect the resilient force of leaf springs on the one side of the direction of the X-coordinate as well as on the one side of the direction of the Y-coordinate. Thus, even on the assumption that the levers are tilted only in the direction of the X-coordinate, a position where the spherical member comes in contact with a contact member when the latter is tilted in the direction of the Y-coordinate is dislocated as they are tilted. The result is that the glass electrode is caused to move finely while scribing a curved track as the levers are tilted, even on the assumption that they are tilted only in the X-direction. This leads to the same problem as mentioned above that they do not perform fine linear movement. Such a problem arises likewise in a case where the levers are tilted only in the Y-direction.

On the other hand, an apparatus of the type using a plurality of micro-hydraulic cylinders has a problem in that the environmental temperature should be kept constant in order to assure that the biological electricity is extracted from a cell for a long period of time, because as an environmental temperature varies, oil in the micro-hydraulic cylinders expands thermally and thereby a glass electrode moves unintentionally to an offset position.

Further, an apparatus of the electrical type has a problem in that due to the fact that an intensity of biological electricity to be extracted from a cell is very weak, exact measurements can not be achieved under the influence of electric induction and magnetic induction caused when step motors are turned on.

SUMMARY OF THE INVENTION

The present invention has been made with the foregoing background in mind and its object resides in providing an apparatus for finely actuating a glass or the like tool which assures that the glass electrode can be finely displaced without any hindrance in the direction of the X-coordinate, in the direction of the Y-coordinate and in the direction of the Z-coordinate.

Another object of the present invention is to provide an apparatus for finely actuating a glass electrode or the like tool which assures that a position of the glass electrode is not dislocated unintentionally irrespective of variation of an environmental temperature.

Another object of the present invention is to provide an apparatus for finely actuating a glass electrode or the like tool which assures that exact measurements can be achieved even under the influence of electric induction and magnetic induction.

To accomplish the above objects, the present invention provides an apparatus for finely actuating a glass electrode or the like tool comprising a movable portion adapted to be vertically displaced with the aid of a vertical actuating mechanism including a combination of rack with pinion, a Y-coordinate slider mounted on the movable portion to freely slide in the vertical direction as viewed from the above, a X-coordinate slider mounted on the Y-coordinate slider to freely slide in the lateral direction relative to the direction of movement of the Y-coordinate slider, the X-coordinate slider serving as an output side, a Y-coordinate thrusting rod and a X-coordinate thrusting rod disposed in the movable portion to move forwardly and backwardly by rotating their knob, a Y-coordinate lever rod and a X-coordinate lever rod disposed between the Y-coordinate slider and the Y-coordinate thrusting rod as well as between the X-coordinate slider and the X-coordinate thrusting rod to assure that a lever ratio is reduced to a fraction of the ration, and two return springs, one of them being resiliently bridged between the movable portion and the Y-coordinate slider and the other one being resiliently bridged between the Y-coordinate slider and the X-coordinate slider.

According to the present invention, the movable portion is first displaced in the vertical direction with the aid of the vertical actuating mechanism in order that the glass electrode is correctly located in the direction of height (in the direction of the Z-coordinate), while the glass electrode is firmly mounted on the X-coordinate slider serving as a final stage. Then, the X-coordinate thrusting rod thrusts the X-coordinate lever rod at one end of the latter so that the other end of the X-coordinate lever rod finely displaces the X-coordinate slider in the lateral direction (in the direction of the X-coordinate) in dependence on a given lever ratio. On the other hand, the Y-coordinate thrusting rod thrusts the Y-coordinate lever rod at one end of the latter so that the other end of the Y-coordinate lever rod finely displaces the Y-coordinate slider in the vertical direction (in the direction of the Y-coordinate) in dependence on a given lever ratio. Thus, the glass electrode can be finely displaced in the direction of the X-coordinate as well as in the direction of the Y-coordinate as required.

Other objects, features and advantages of the present invention will become readily apparent from a reading of the following description which has been made in conjunction with the accompanying drawings.

DESCRIPTION OF THE PREFERRED EMBODIMENT

Now, the present invention will be described in a greater detail hereunder with reference to the accompanying drawings which illustrate an apparatus for finely actuating a glass electrode or the like tool in accordance with an embodiment thereof.

Figure 1:
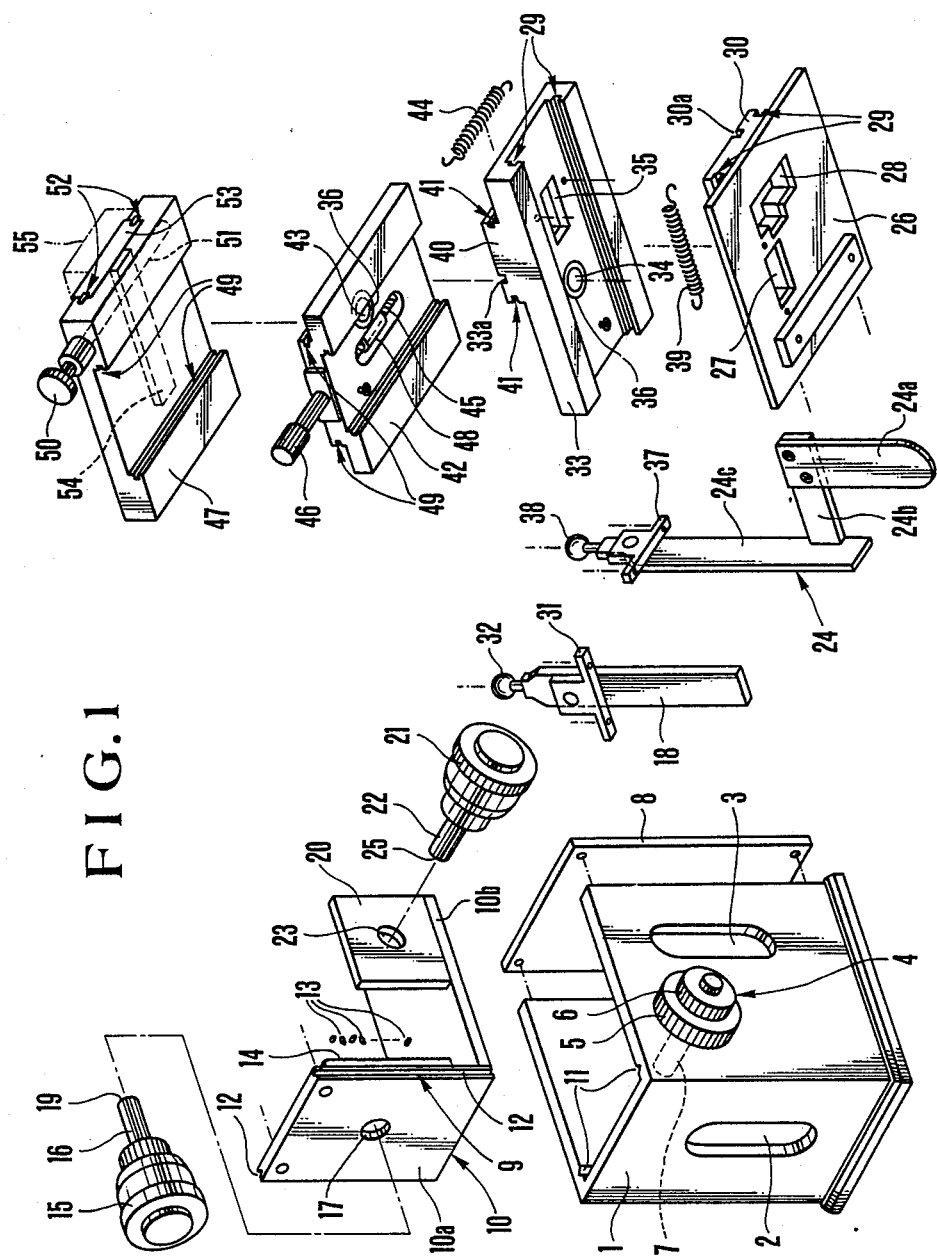
FIG. 1 is a perspective view illustrating an apparatus for finely actuating a glass electrode or the like tool in accordance with an embodiment of the invention, shown in a disassembled state.

In FIG. 1, reference numeral 1 designates a casing of which the upper end and fore end are opened to the outside. The casing 1 is formed with elongated holes 2 and 3 on a rear wall and one side wall thereof. A vertical actuating mechanism 4 operable in the Z-coordinate direction is attached to the one side wall of the casing 1. The mechanism 4 includes a rough adjustment knob 5 and a fine adjustment knob 6. Specifically, the knob 5 is so designed that a ratio of number of rotations of the knob 5 to number of rotations of an output shaft is set to 1:1, while the knob 6 has a substantially reduced ratio with respect to rotation of the output shaft by utilizing a group of gears such as a flexible gear or the like. As will be best seen in FIG. 3, a pinion 7 serving as an output shaft is exposed to the interior of the casing 1.

Figure 2:
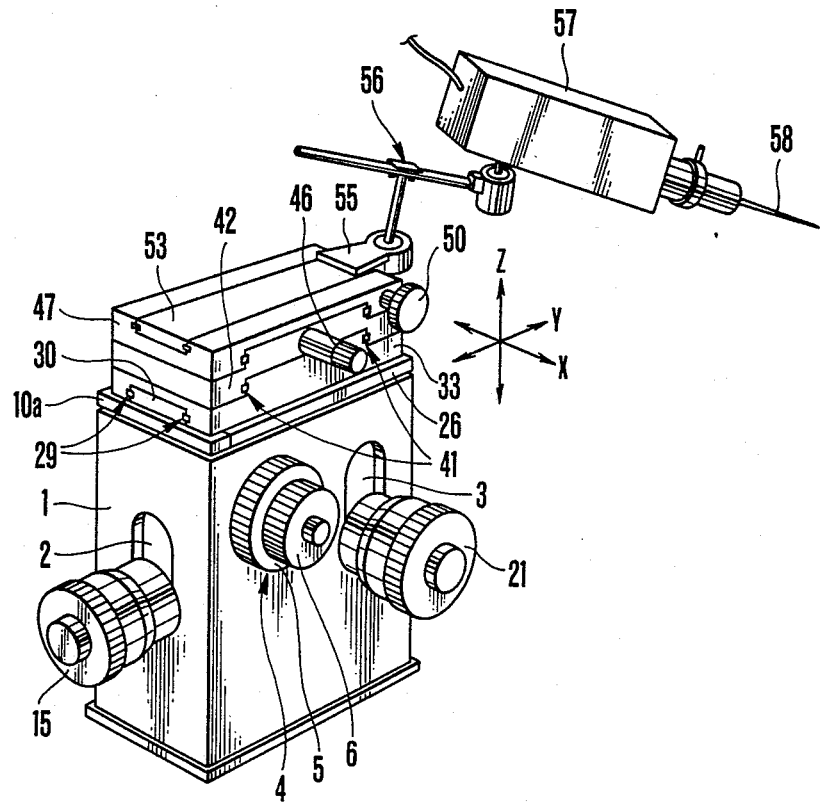
FIG. 2 is a perspective view of the apparatus in FIG. 1, particularly illustrating the whole apparatus in an operative state.

A front plate 8 is fixedly secured to the fore end of the casing by means of screws. A L-shaped movable portion 10 is vertically displaceably accommodated in the casing 1 with the aid of linear motion bearings 9. The linear motion bearing 9 is constructed in such a manner that V-shaped guide grooves 11 and 12 are formed along an end face of a vertically extending wall 10a of the movable portion 10 and an inner surface of the side wall of the casing 1 located opposite to the end face of the wall 10a. A number of small rollers 13 are interposed between both the guide grooves 11 and 12 one above another with the direction of their axes alternately differing by an angle of 90 degrees. A rack 14 is fixedly secured to the inner surface of the wall 10a of the movable portion 10 so that it meshes with the pinion 7. A Y-coordinate adjustment knob 15 is attached to the wall 10a of the movable portion 10 and a Y-coordinate thrusting rod 16 projecting from the knob 15 is inserted into the interior of the casing 1 through a hole 17. The rod 16 is fitted with a steel ball 19 at the foremost end thereof to come in point contact with a Y-coordinate lever rod 18 which will be described later. As is apparent from the drawings, the knob 15 projects outwardly from the casing 1 through the elongated hole 2. A support plate 20 stands upright on the bottom wall 10b of the movable portion 10 so that a X-coordinate adjustment knob 21 is attached to the support plate 20. A x-coordinate thrusting rod 22 projecting from the knob 21 is inserted into the interior of the casing 1 through a hole 23 on the support plate 20. The rod 22 is likewise fitted with a steel ball 25 at the foremost end thereof to come in point contact with a X-coordinate lever rod 24 which will be described later. The knob 15 projects outwardly of the casing 1 through the elongated hole 3. One end of an upper plate 26 is fixed to the inner surface at the upper end of the wall 10a of the movable portion 10 by means of screws. The upper plate 26 is formed with a substantially rectangular hole 27 through which the Y-coordinate lever rod 18 is inserted and a substantially T-shaped hole 28 through which the X-coordinate lever rod 24 is inserted. Further, the upper plate 26 has a base board 30 fixedly mounted thereon and linear motion bearings 29 are disposed on both side ends of the base board 30. Of course, the base board 30 may be made integral with the upper plate 26. The linear motion bearing 29 is constructed in the same manner as the aforementioned one and comprises a number of small rollers interposed between the two oppositely located guide grooves. A support member 31 for the Y-coordinate lever rod 18 is firmly attached along one edge of the rectangular hole 27 by means of screws. The Y-coordinate lever rod 18 is fixedly fitted with a steel ball 32 at the uppermost end thereof. The support member 31 is turnably held on the Y-coordinate lever rod 18 at a position where a distance between a center of the steel ball 32 and a center of turning movement of the support member 31 is determined equal to one-fifth of a length of the Y-coordinate lever rod 18, that is, a position where a lever ratio is set to 1:5. A Y-coordinate slider 33 is slidably fitted to the upper plate 26 with the aid of the linear motion bearings 29. The Y-coordinate slider 33 is formed with a blind hole 34 having a properly determined depth in which the steel ball 32 on the Y-coordinate lever rod 18 is received and a rectangular hole 35 through which the X-coordinate lever rod 24 is inserted. A slip ring 36 made of synthetic resin is fitted around the periphery of the blind hole 34 in order to assure smooth slidable movement of the steel ball 32. A support member 37 for the X-coordinate lever rod 24 is fixedly secured to one edge of the rectangular hole 27 by means of screws. The X-coordinate lever rod 24 is composed of a first lever rod 24a and a second lever rod 24c which is connected to the first lever rod 24a via a connecting rod 24b. The second rod 24c is turnably held on the support member 37. The second lever rod 24c is provided with a steel ball 38 at the end thereof. The second lever rod 24c is turnably held on the support member 37 at a position where a distance between a center of the steel ball 38 and a center of turning movement of the second lever rod 24c is determined to be one-fifth of a height of the X-coordinate lever rod 24 as measured from a position where the first lever rod 24a is thrust by the X-coordinate thrusting rod 22. This means that the X-coordinate lever rod 24 has a lever ratio of 1:5 too. A return spring 39 is resiliently bridged between the upper plate 26 and the Y-coordinate slider 33. Bridging of the return spring 39 is achieved using a screw on the upper plate 26 and a screw on the Y-coordinate slider 33 and the return spring 39 is accommodated in a relief groove 30a on the base board 30. A holding board 40 is made integral with the Y-coordinate slider 33 while projecting above the latter and an arrangement is so made that linear motion bearings 41 are disposed on both side ends of the holding board 40. The linear motion bearing 41 is constructed by a large number of small rollers which are interposed between two oppositely located guide grooves in the same manner as the aforementioned one. A X-coordinate slider 42 is slidably mounted on the holding board 40 so as to smoothly slide in the direction of the X-coordinate with the aid of the linear motion bearings 41. The X-coordinate slider 42 is formed with a blind hole 43 having a predetermined depth and a slip ring 36 is fitted around the periphery of the blind hole 43 in the same manner as the aforementioned one. The steel ball 38 is received in the blind hole 43. A return spring 44 is likewise bridged between the Y-coordinate slider 33 and the X-coordinate slider 42 by means of screws. The return spring 44 is accommodated in a relief groove 33a on the Y-coordinate slider 33. The X-coordinate slider 42 is rotatably provided with a screw rod 45 for roughly displacing it in the direction of the X-coordinate and a knob 46 is attached to the screw rod 45. The screw rod 45 is threadably engaged to a female-threaded sleeve 48 which is fixedly secured to a slider 47 adapted to roughly slide in the direction of the X-coordinate. The slider 47 is slidably mounted on the slider 42 so as to smoothly slide in the direction of the X-coordinate with the aid of linear motion bearings 49. A pinion 51 with a knob 50 for rough adjustment in the direction of the Y-coordinate attached thereto is rotatably supported on the slider 47. A slider 53 adapted to roughly slide in the direction of the Y-coordinate is slidably attached to the slider 47 so as to smoothly slide in the direction of the Y-coordinate with the aid of linear motion bearings 52. The slider 53 is provided with a rack 54 adapted to mesh with the pinion 51 which is supported on the slider 47. As shown in FIG. 2, a probe 57 is attached to the slider 53 via a bracket 55 and a ball joint mechanism 56. The probe 57 is provided with a glass electrode 58 which is filled with electrolyte.

It should be noted that the X-coordinate rough actuating mechanism comprising the rod 45, the female-threaded sleeve 48 and others as well as the Y-coordinate rough actuating mechanism comprising the pinion 51, the rack 54 and others are constructed by utilizing a hitherto known structure. Further, it should be noted that the return springs 39 and 44 are effective for preventing backlash of the Y-coordinate slider 33 and the X-coordinate slider 42.

Next, operation of the apparatus as constructed in the aforementioned manner will be described below.

Figure 3:
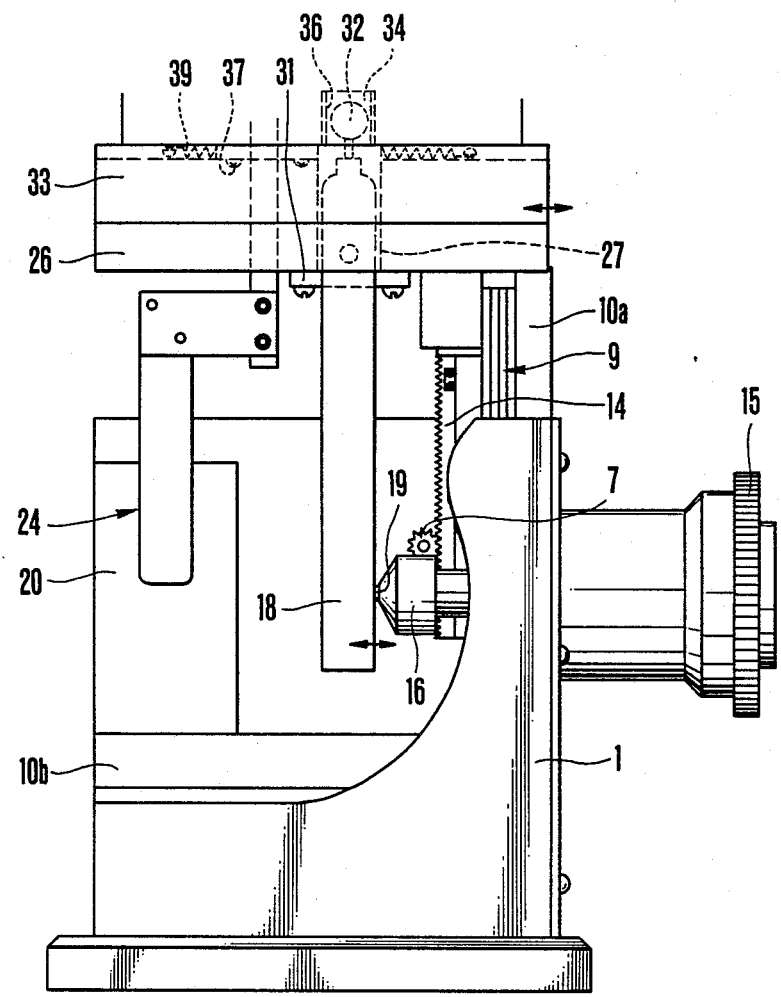
FIG. 3 is a view illustrating the apparatus when fine actuation is carried out in the direction of the Y-coordinate.
Figure 4:
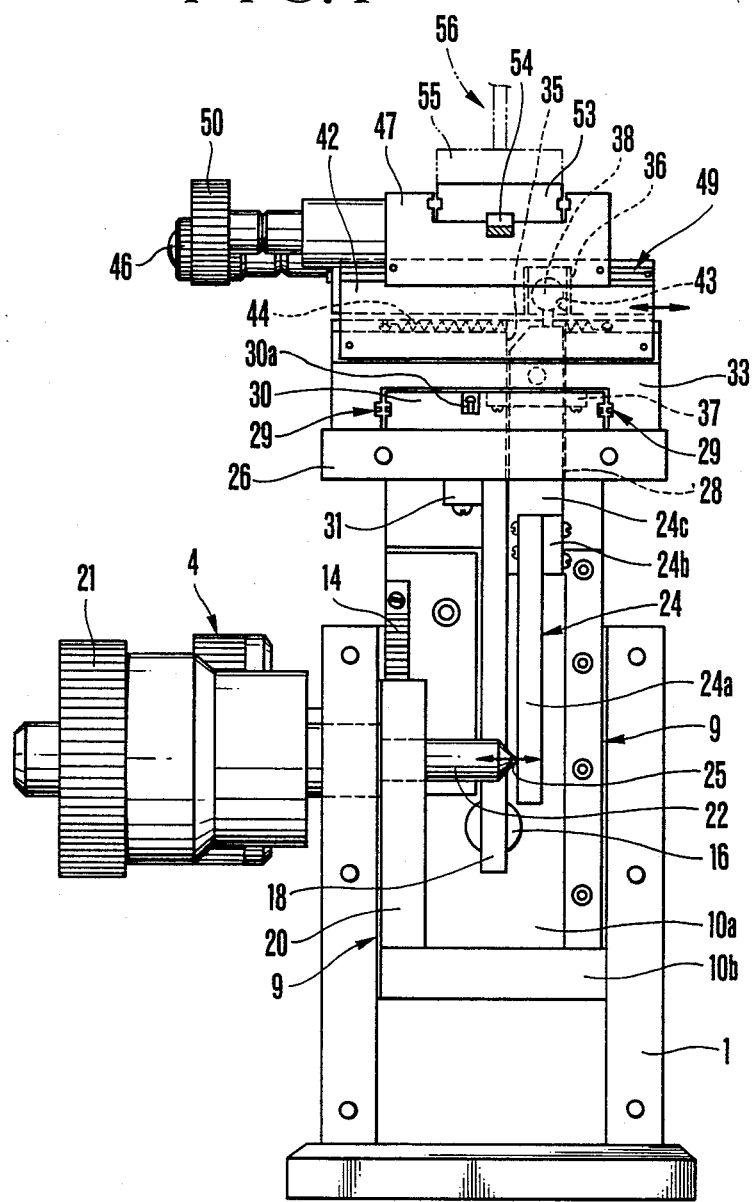
FIG. 4 is a view illustrating the apparatus when fine actuation is carried out in the direction of the X-coordinate.

When a height of the glass electrode 58 (as seen in the direction of the Z-coordinate) is to be determined, a rough position is first determined by rotating the rough adjustment knob 5 for the vertical actuating mechanism and an exact position is then determined by rotating the fine adjustment knob 6. Gear ratios are set in such a manner that the movable portion 10 is vertically displaced by a distance of about 2 mm owing to meshing of the pinion 7 with the rack 14 when the knob 5 is rotated by one revolution, while it is vertically displaced by a distance of about 20 microns when the knob 6 is rotated by one revolution. With respect to rough displacement in the direction of the Y-coordinate, the Y-coordinate rough actuating slider 53 is roughly displaced in the direction of the Y-direction by rotating the Y-coordinate adjustment knob 50 so that a position of the glass electrode 58 as seen in the direction of the Y-coordinate is approximately determined by rough displacement of the slider 53 in the direction of the Y-coordinate owing to meshing of the pinion 51 with the rack 54. With respect to rough displacement in the direction of the X-coordinate, the slider 47 is roughly displaced in the direction of the X-coordinate by threadable engagement of the screw rod 45 to the sleeve 48 so that a position of the glass electrode 58 as seen in the direction of the X-coordinate is determined approximately. Next, when the glass electrode 58 is to be finely displaced in the direction of the Y-coordinate, the Y-coordinate adjustment knob 15 is rotated. This causes the Y-coordinate thrusting rod 16 to thrust the Y-coordinate lever rod 18, as shown in FIG. 3. Then, the lever rod 18 is caused to turn about the pivotal axis on the support member 31 under the effect of thrusting force and thereby the Y-coordinate slider 33 is thrusted against resilient force of the return spring 39. Since a lever ratio of the lever rod 18 is set to 1:5, an amount of thrusting movement of the slider 33 is reduced to one-fifth of an amount of thrusting movement of the lever rod 18. This enables the slider 33 to finely move in direction of the Y-coordinate whereby a position of the glass electrode 58, as seen in the direction of the Y-coordinate, can be exactly determined on the order of microns. On the contrary, when the rod 16 is retracted in the reverse direction, the lever rod 18 is displaced backwardly along with the slider 33 under the effect of resilient force of the return spring 39. When the glass electrode 58 is to be finely displaced in the direction of the X-coordinate, the X-coordinate adjustment knob 21 is rotated so that the X-coordinate thrusting rod 22 thrusts the X-coordinate lever rod 24. Since a lever ratio of the lever rod 24 is likewise set to 1:5, the X-coordinate slider 42 is finely displaced in the direction of the X-coordinate by a distance which is reduced by the same rate as the lever ratio with respect to a distance of turning movement of the lever rod 24. This enables the glass electrode 58 to be finely displaced in the direction of the X-coordinate until it is exactly located at a predetermined position. On the contrary, when the rod 22 is retracted in the reverse direction, the lever rod 24 is returned along with the slider 42 under the effect of resilient force of the return spring 44.

As described above, the glass electrode 58 is located at a predetermined channel on the cell membrane to come in contact with it whereby the probe 57 detects the biological electricity from the cell through the predetermined channel for a long period of time via an electrolyte filled in the glass electrode 58 in accordance with a so-called patch clamp system. The detected biological electricity is fed to other apparatus (not shown) to obtain research data.

While the present invention has been described above merely with respect to a single preferred embodiment, it should of course be understood that it should not be limited only to this. Alternatively, various changes or modifications may be suitably made without any departure from the spirit and scope of the invention as defined by the appended claim.

What is claimed is:

1. An apparatus for adjusting the position of an instrument for the purpose of acting on a cell, said apparatus comprising:
   a casing having at least one surface open;
   movable portion means mounted in said casing and being provided for moving in the vertical direction;
   first adjustment means for adjusting the vertical position of the movable portion means;
   Y-coordinate actuating slider means mounted on said movable portion means for freely sliding along a first lateral direction perpendicular to the vertical direction;
   second adjustment means for adjusting the position of the Y-coordinate actuating slider means along the first lateral direction;
   X-coordinate actuating slider means mounted on said Y-coordinate actuating slider means for freely sliding along a second lateral direction perpendicular to both the first lateral direction and to the vertical direction;
   third adjustment means for adjusting the position of the X-coordinate actuating slider means along the second lateral direction;
   X-coordinate rough actuating slider means mounted on said X-coordinate actuating slider means for freely sliding along the second lateral direction;
   forth adjustment means for adjusting the position of the X-coordinate rough actuating slider means along the second lateral direction;
   Y-coordinate rough actuating slider means mounted on said X-coordinate rough actuating slider means for freely sliding along the first lateral direction; and
   fifth adjustment means for adjusting the position of the Y-coordinate rough actuating slider means along the first lateral direction.

2. An apparatus as in claim 1, further comprising:
   a bracket attached to said Y-coordinate rough actuating slider means and an instrument attached to said bracket.

3. An apparatus as in claim 2, wherein said instrument comprises a glass electrode.

4. An apparatus as in claim 1, said movable portion means comprising an L-shaped structure having linear motion bearings and a rack fixedly secured along one surface and an upper plate secured along a second surface of said L-shaped structure, said upper plate having two opposed linear motion bearings formed on an upper surface and having first and second holes.

5. An apparatus as in claim 4, said first adjusting means comprising: a pinion which meshes with the rack fixedly secured on said L-shaped structure; an output shaft connected at one end to said pinion; and both fine and rough adjustment knobs coupled to the other end of said output shaft, one rotation of said rough adjustment knob substantially resulting in one rotation of said output shaft and one rotation of said fine adjustment knob resulting in less than one rotation of said output shaft.

6. An apparatus as in claim 5, said Y-coordinate actuating slider means comprising: a plate having a through hole, a recessed portion, and two opposed linear motion bearings formed integrally on one side of said plate which cooperatively engage with the two opposed linear motion bearings formed on the upper surface of said upper plate and a holding board formed integrally on the other side of said plate, said holding board having two opposed linear motion bearings formed on an upper surface.

7. An apparatus as in claim 6, said second adjustment means comprising: a lever rod which passes through the first hole in said upper plate and which engages at one end with the recessed portion of said plate; a thrusting rod which at one end contacts with the other end of said lever rod; and a knob connected to the other end of said thrusting rod, said knob being turned in both the clockwise and counter-clockwise directions for moving the Y-coordinate actuating slider means through cooperative movement of said thrusting rod and lever rod.

8. An apparatus as in claim 7, said X-coordinate actuating slider means comprising: a second plate having a recessed portion, two opposed linear motion bearings integrally formed on one side of said second plate which cooperatively engage with the two opposed linear motion bearings on said holding board of said Y-coordinate actuating slider means and a holding board formed integrally on the other side of said second plate, said holding board having two opposed linear motion bearings formed on an upper surface.

9. An apparatus as in claim 8, said third adjustment means comprising: a lever rod which passes through the second hole in said upper plate and the hole in said plate and which engages at one end with the recessed portion of said second plate; a thrusting rod which at one end contacts with the other end of said lever rod; and a knob connected to the other end of said thrusting rod, said knob being turned in both the clockwise and counter-clockwise directions for moving the X-coordinate actuating slider means through cooperative movement of said thrusting rod and lever rod.

10. An apparatus as in claim 9, said X-coordinate rough actuating slider means comprising: a third plate having two opposed linear motion bearings integrally formed on one side, which cooperatively engage with the two opposed linear motion bearing on said holding board of said X-coordinate actuating slider means, and having two opposed linear motion bearings integrally formed on the other side.

11. An apparatus as in claim 10, said fourth adjustment means comprising: a screw rod mounted within a central opening in said third plate; a knob attached at one end to said screw rod; a sleeve carried by said screw rod, said sleeve being connected to said third plate; said knob being turned in both the clockwise and counter-clockwise directions for moving the sleeve along the screw rod and thereby moving the X-coordinate rough actuating slider means.

12. An apparatus as in claim 11, said Y-coordinate rough actuating slider means comprising: a fourth plate having two opposed linear motion bearings which cooperatively engage with the two opposed linear motion bearings formed on the other side of said third plate, and a rack mounted on said fourth plate.

13. An apparatus as in claim 12, said fifth adjustment means comprising: a pinion which engages with the rack mounted on said fourth plate; and a knob connected to said pinion, said knob being turned in both the clockwise and counter-clockwise directions for moving the Y-coordinate rough actuating slider means through cooperative movement of said rack and pinion.

14. An apparatus as in claim 13, further comprising a spring resiliently bridged between said upper plate and said Y-coordinate actuating slider.

15. An apparatus as in claim 14, further comprising a second spring bridged between said Y-coordinate actuating slider and said X-coordinate actuating slider.

16. An apparatus as in claim 15, further comprising: a bracket attached to said Y-coordinate rough actuating slider means and an instrument attached to said bracket.

17. An apparatus as in claim 16, wherein said instrument comprises a glass electrode.

* * * * *